(12) United States Patent
Wingeier et al.

(10) Patent No.: US 9,101,771 B2
(45) Date of Patent: Aug. 11, 2015

(54) SYSTEM AND METHOD FOR OPTIMIZING ENERGY USE AND DELIVERED CURRENT IN AN IMPLANTABLE DEVICE

(71) Applicant: NeuroPace, Inc., Mountain View, CA (US)

(72) Inventors: Brett D Wingeier, San Francisco, CA (US); Suresh Gurunathan, Palo Alto, CA (US); Craig Baysinger, Livermore, CA (US)

(73) Assignee: NeuroPace, Inc., Mountain View, CA (US)

( * ) Notice: Subject to any disclaimer, the term of this patent is extended or adjusted under 35 U.S.C. 154(b) by 0 days.

(21) Appl. No.: 14/211,217

(22) Filed: Mar. 14, 2014

(65) Prior Publication Data

US 2014/0277289 A1    Sep. 18, 2014

Related U.S. Application Data

(60) Provisional application No. 61/790,920, filed on Mar. 15, 2013.

(51) Int. Cl.
*A61N 1/00* (2006.01)
*A61N 1/36* (2006.01)
*A61N 1/378* (2006.01)

(52) U.S. Cl.
CPC ............. *A61N 1/36146* (2013.01); *A61N 1/378* (2013.01)

(58) Field of Classification Search
CPC ............ A61N 1/36146; A61N 1/3615; A61N 1/36128; A61N 1/378
See application file for complete search history.

(56) References Cited

U.S. PATENT DOCUMENTS

| | | | |
|---|---|---|---|
| 6,016,449 A | 1/2000 | Fischell | |
| 6,516,227 B1 * | 2/2003 | Meadows et al. | 607/46 |
| 6,690,974 B2 | 2/2004 | Archer | |
| 6,810,285 B2 | 10/2004 | Pless | |
| 8,588,931 B2 * | 11/2013 | Halpern et al. | 607/72 |

* cited by examiner

*Primary Examiner* — George Manuel
(74) *Attorney, Agent, or Firm* — Arent Fox LLP (57) ABSTRACT

A system and method for automatically adjusting the value of a parameter defined to manage and control the resources recruited by an implantable medical device to supply power or the device to deliver an instance of an electrical stimulation therapy to a patient. In embodiments, the parameter corresponds to a number of capacitors the discharge of which supplies the power to deliver a stimulation therapy at a programmed amplitude. Whenever the circumstances prevent the programmed amplitude from being delivered, the system and method automatically adjust the resource-controlling parameter to use the minimum power to achieve the desired (programmed) amplitude or as close as possible to that programmed amplitude. Some embodiments additionally include using another parameter (a equivalent amplitude parameter) to balance the charge delivered through multiple pathways in parallel sourced from a single reservoir of power.

18 Claims, 8 Drawing Sheets

SYSTEM AND METHOD FOR OPTIMIZING ENERGY USE AND DELIVERED CURRENT IN AN IMPLANTABLE DEVICE

CROSS-REFERENCE TO RELATED APPLICATION(S)

This application claims the benefit of U.S. Provisional Application Ser. No. 61/790,920, entitled "System and Method for Optimizing Energy Use and Delivered Current in an Implantable Device," filed Mar. 15, 2013, which is expressly incorporated by reference herein in its entirety.

BACKGROUND

1. Field

The present technology relates generally to devices, methods and systems for managing the power resources in an active implantable medical device, especially an active implantable medical device configured to deliver a form of electrical stimulation therapy to a patient.

2. Background

Active implantable medical devices such as neurostimulators (also referred to as implantable pulse generators or "IPG"s) are known that can be configured to deliver stimulation to a neural target in a patient (e.g., neural tissue) in different ways, such as by regulating voltage, current or charge. Programmable parameters are used to control the stimulation that the implant delivers. Sometimes, and for various reasons, the neurostimulator will not be able to deliver to the patient the stimulation the device is programmed to deliver. Embodiments described herein are concerned with that condition of active implantable medical devices.

SUMMARY

An active implantable medical device optimizes power usage during delivery of electrical stimulation to a human patient. The device detects a first insufficient charge condition when an amplitude of the stimulation the implantable medical device is programmed to deliver cannot in fact be delivered. The device determines whether a parameter associated with the control of a power source available to deliver an instance of stimulation therapy can be adjusted to improve the charge condition.

If the power-control parameter can be adjusted, the device adjusts the power-control parameter in a first direction until an insufficient charge is no longer detected. The power-control parameter may be a capacitor mode parameter that corresponds to a number of capacitors used to provide the power for any given instance of stimulation therapy. In this case, the first direction of the power-control parameter corresponds to an increase in the number of capacitors.

If the power-control parameter cannot be adjusted, the device determines whether a working setting of the amplitude of the stimulation exceeds a programmed minimum setting. If the working setting exceeds the minimum setting, then the device adjusts the working setting in a first direction until an insufficient charge is no longer detected. The first direction of the working setting may correspond to a decrease in the working setting. For example, if the working setting relates to an amount of current to be delivered, the current may be decreased.

The device periodically adjusts one of the power-control parameter and the working setting in a second direction opposite the respective first direction. Adjustments in the second direction may be performed until another insufficient charge is encountered. In some instances, the working setting is adjusted in the second direction when the working setting is different from the programmed minimum setting. In other instances, the power-control parameter is adjusted in the second direction when the working setting is identical to the programmed minimum setting and the power-control parameter exceeds a programmed minimum.

BRIEF DESCRIPTION OF THE DRAWINGS

The accompanying drawings, which are incorporated in and form a part of this specification, illustrate and serve to explain the principles of embodiments in conjunction with the description. Unless specifically noted, the drawings referred to in this description should be understood as not being drawn to scale.

DETAILED DESCRIPTION

Neurostimulators are often provided with a variety of parameters programmable by a user that will govern the form of stimulation the implantable medical device will generate when commanded to do so. These parameters may vary depending on the type of stimulation the implant is configured to deliver. When the neurostimulator is configured to deliver electrical stimulation, the programmable parameters may include parameters which control the shape of the stimulation waveform (e.g., pulsatile, non-pulsatile (e.g., sine wave) or direct current).

For pulsatile waveforms, other parameters may include the amplitude of the stimulation (e.g., in amps), the pulse width (e.g., in microseconds or milliseconds), whether the first phase of a pulse is the same, albeit perhaps with opposite polarity, as a second phase of the pulse, or how often pulses are delivered (interpulse interval, or in the inverse, frequency).

Still other parameters may be programmable to define how many pulses will be delivered in a given instance of a stimulation therapy, e.g., a "burst" of stimulation may be defined to include a certain number and kind of pulses, or may be defined as continuous delivery of a certain kind of pulses for an indeterminate interval, and a given instance of a stimulation therapy may be defined to include one or more bursts. When multiple bursts are to be delivered for a given stimulation therapy, another parameter may allow a user to program a time delay between bursts (e.g., an interburst interval). In some neurostimulation systems, parameters may be available that allow a user to program a stimulation therapy to be triggered when the neurostimulator detects a pattern or "event" in electrographic signals being monitored from the patient.

These parameters may include timing the delivery of stimulation based on a characteristic of the monitored signals or on a characteristic of a pattern or event detected in the monitored signals. Other parameters for adapting a given stimulation therapy to the occurrence of a detected pattern or event may be available for a user to program, such as adapting a frequency of a stimulation therapy based on a frequency that characterizes the monitored signals or an event detected in the monitored signals.

Neurostimulation systems including an active implantable medical device as well as other implantable components (brain leads for sensing and delivering stimulation) and external components, such as a physician programmer are described in, inter alia, U.S. Pat. No. 6,016,449 to Fischell, et al. for "System for Treatment of Neurological Disorders", issued Jan. 18, 2000, U.S. Pat. No. 6,810,285 to Pless et al. for "Seizure Sensing and Detection Using An Implantable Device," issued Oct. 24, 2004, and U.S. Pat. No. 6,690,974 to Archer et al. for "Stimulation Signal Generator for an Implantable Device" issued Feb. 10, 2004. Each of the '449, '285 and '974 patents is hereby incorporated by reference in the entirety.

Various aspects of the disclosure will be described more fully hereinafter with reference to the accompanying drawings. This disclosure may, however, be embodied in many different forms by those skilled in the art and should not be construed as limited to any specific structure or function presented herein. Rather, these aspects are provided so that this disclosure will be thorough and complete, and will fully convey the scope of the disclosure to those skilled in the art. Based on the teachings herein, one skilled in the art should appreciate that the scope of the disclosure is intended to cover any aspect of this disclosure, whether implemented independently of or combined with any other aspect of the disclosure. For example, an apparatus may be implemented or a method may be practiced using any number of the aspects set forth herein. In addition, the scope of the disclosure is intended to cover such an apparatus or method which is practiced using other structure and/or functionality in addition to or instead of other aspects of this disclosure. It should be understood that any aspect of the disclosure disclosed herein may be embodied by one or more elements of a claim.

The concepts disclosed may be implemented in hardware or software that is executed on a hardware platform. The hardware or hardware platform may be a general purpose processor, a digital signal processor (DSP), an application specific integrated circuit (ASIC), a field programmable gate array (FPGA) or other programmable logic component, discrete gate or transistor logic, discrete hardware components, or any combination thereof, or any other suitable component designed to perform the functions described herein. A general-purpose processor may be a microprocessor, but in the alternative, the processor may be any conventional processor, controller, microcontroller, or state machine. A processor may also be implemented as a combination of computing components, e.g., a combination of a DSP and a microprocessor, a plurality of microprocessors, one or more microprocessors in conjunction with a DSP, or any other such configuration.

Software shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise. The software may reside on a computer-readable medium. A computer-readable medium may include, by way of example, a magnetic storage device (e.g., hard disk, floppy disk, magnetic strip), an optical disk (e.g., compact disk (CD), digital versatile disk (DVD)), a smart card, a flash memory device (e.g., card, stick, key drive), random access memory (RAM), read only memory (ROM), programmable ROM (PROM), erasable PROM (EPROM), electrically erasable PROM (EEPROM), a general register, or any other suitable non-transitory medium for storing software.

Figure 1:
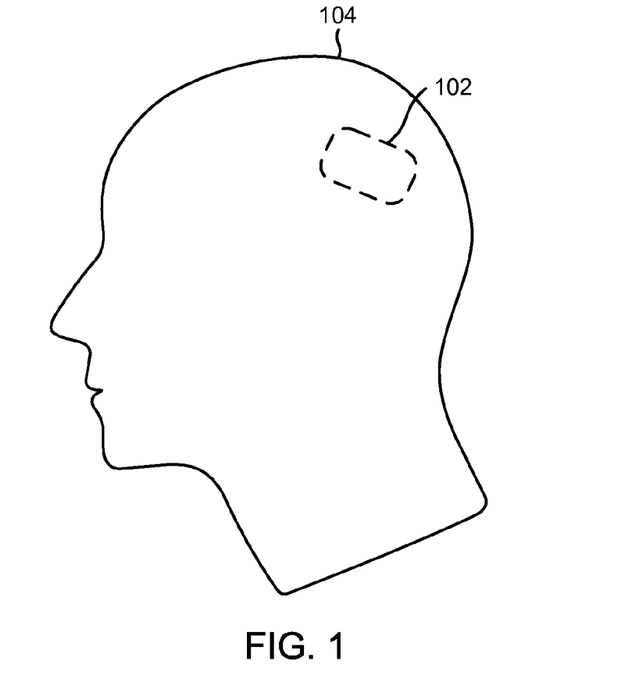
FIG. 1 is a schematic illustration of a patient's head showing the placement of an implantable medical device.

With reference to FIG. 1, an exemplary active implantable medical device 102 is shown implanted in a patient 104. In one configuration, the implantable medical device 102 includes a small self-contained brainwave detecting device. As the term is used herein, a brainwave detecting or recording device is a device capable of detecting or predicting ictal activity (or other neurological events) for providing data useful in the diagnosis of a neurological disorder. Further, the term recording device, as used herein, is a device that can either record neurological signals, such as EEG signals, or detect and analyze EEG signals and create a log of such an analysis.

The implantable medical device 102 may be configured to detect or predict neurological events that have a representative electrographic signature. For example, the implantable medical device 102 may be responsive to epileptic seizures. It should, however, be recognized that it is also possible to respond to other types of neurological disorders, such as movement disorders (e.g. the tremors characterizing Parkinson's disease), migraine headaches, chronic pain, and neuropsychiatric disorders such as depression.

Figure 2:
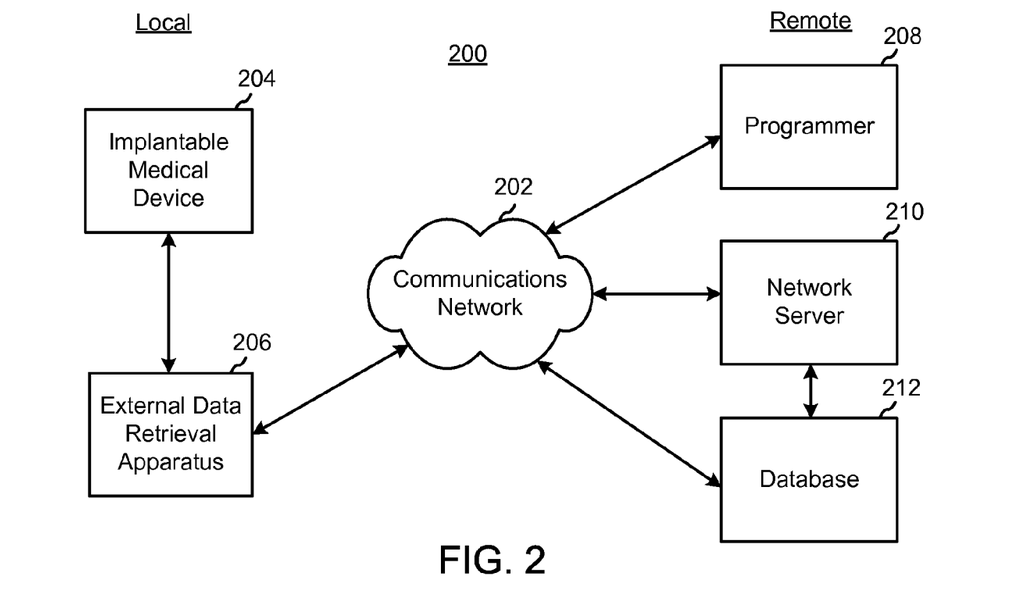
FIG. 2 is a block diagram of a system for providing communication between local medical devices and remote system components.

With reference to FIG. 2, an exemplary patient monitoring system 200 is illustrated. The patient monitoring system 200 includes local components and remote components that communicate through a communications network 202, such as the Internet. Local components are located in the vicinity of the patient, such as the patient's residence, and may include an implantable medical device 204, and a local device 206, referred to herein as a data retrieval apparatus. Remote components are located a significant distance from the patient, such as at a hospital or care provider's office. Remote components may include, for example, a programmer 208, a network server 210 and a database 212.

The programmer 208 is typically operated by medical personnel (such as the patient's treating physician) to control the operation of the implantable medical device 204. In general terms, the programmer 208 functions as a clinical interface to the implantable medical device 204, allowing the implantable medical device parameters to be modified, and for data and/or program code to be uploaded from and downloaded to the implantable medical device.

The database 212 serves as a centralized data repository for all data relevant to the operation of the system 200, and may include clinical data, program code, and more. The network server 210 acts as the primary interface between the database 212 and other devices attached to the communications network 202. Although it might be possible and advantageous in certain circumstances to communicate directly with the database 212, it is generally preferable to configure the network server 210 to receive queries, perform necessary authentication, access the database 212, and respond as necessary, thereby reducing the processing load on the database and also reducing the exposure of the database to network traffic (thereby improving security).

The data retrieval apparatus 206 is configured to receive data from remote components through the communications network 202 and provide it to the implantable medical device 204. Such data may include, for example, program code or instructions from a programmer 208 that affect the operation of the implantable medical device 204. The data retrieval apparatus 206 is also configured to retrieve data from the implantable medical device 204 and to forward it to one or more of the remote components. As described further below, communication between the data retrieval apparatus 202 and the implantable medical device 204 is wireless, and may be in the form of short-range telemetry by inductive coupling or long-range telemetry by RF communications.

Figure 3:
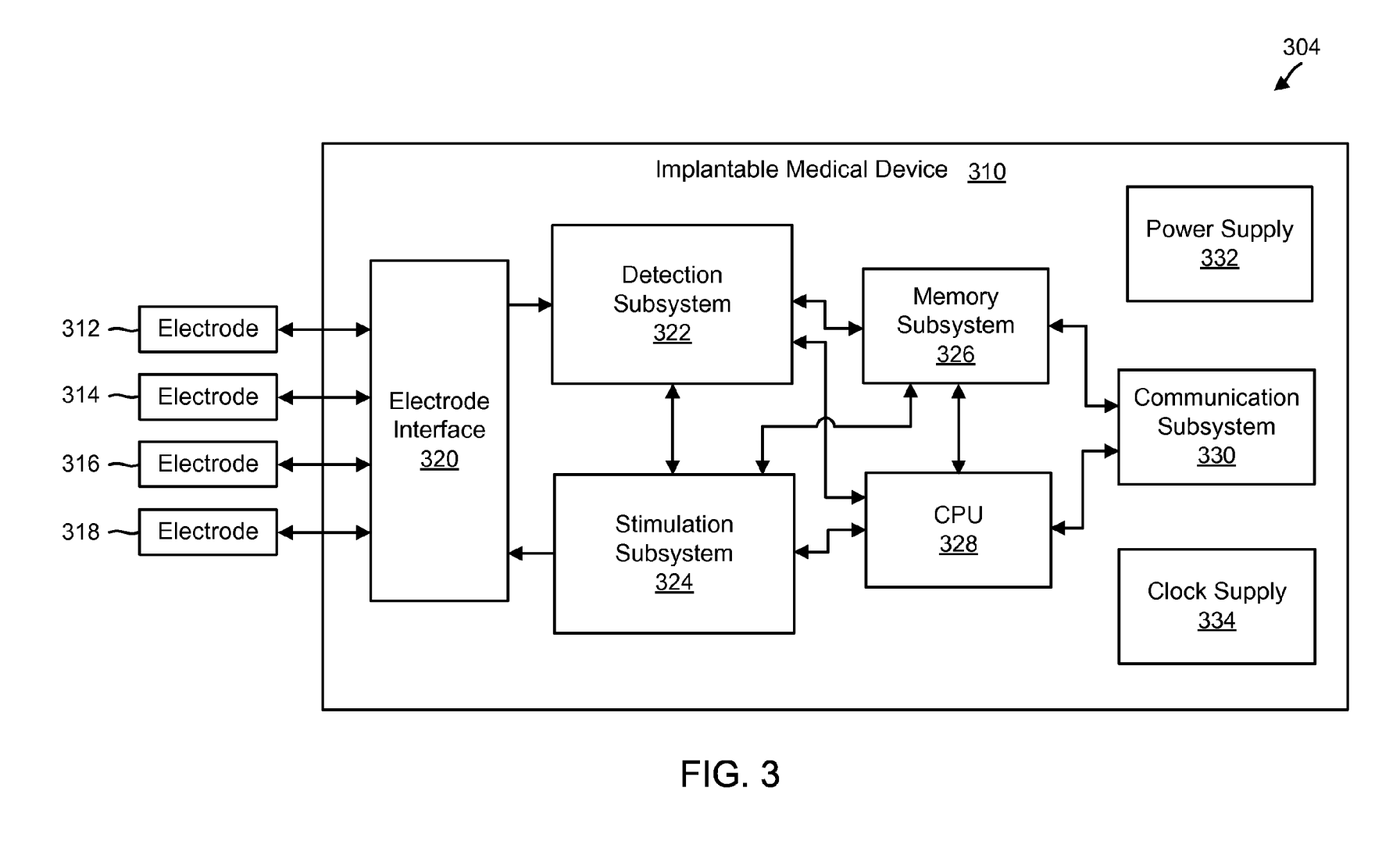
FIG. 3 is a block diagram of an implantable medical device.

An overall block diagram of an implantable medical device 304 used for measurement, detection, and treatment is illustrated in FIG. 3. Inside the housing of the device 304 are several subsystems making up a control module 310. The control module 310 is capable of being coupled to a plurality of electrodes 312, 314, 316, and 318 for sensing and stimulation. Although four electrodes are shown in FIG. 3, it should be recognized that any number is possible.

The electrodes 312-318 are connected to an electrode interface 320. Preferably, the electrode interface is capable of selecting each electrode as required for sensing and stimulation; accordingly the electrode interface is coupled to a detection subsystem 322 and a stimulation subsystem 324. The electrode interface also may provide any other features, capabilities, or aspects, including but not limited to amplification, isolation, and charge-balancing functions, that are required for a proper interface with neurological tissue and not provided by any other subsystem of the implantable medical device 304.

The detection subsystem 322 includes an EEG analyzer function. The EEG analyzer function is adapted to receive EEG signals from the electrodes 312-318, through the electrode interface 320, and to process those EEG signals to identify neurological activity indicative of a seizure, an onset of a seizure, or a precursor to a seizure. One way to implement such EEG analysis functionality is disclosed in detail in U.S. Pat. No. 6,016,449 to Fischell et al., which is hereby incorporated by reference. The detection subsystem may optionally also contain further sensing and detection capabilities, including but not limited to parameters derived from other physiological conditions (such as electrophysiological parameters, temperature, blood pressure, etc.).

The stimulation subsystem 324 is capable of applying electrical stimulation to neurological tissue through the electrodes 312-318. This can be accomplished in any of a number of different manners. For example, it may be advantageous in some circumstances to provide stimulation in the form of a substantially continuous stream of pulses, or on a scheduled basis. Preferably, therapeutic stimulation is provided in response to abnormal events detected by the EEG analyzer function of the detection subsystem 322. As illustrated in FIG. 3, the stimulation subsystem 324 and the EEG analyzer function of the detection subsystem 322 are in communication; this facilitates the ability of stimulation subsystem 324 to provide responsive stimulation as well as an ability of the detection subsystem 322 to blank the amplifiers while stimulation is being performed to minimize stimulation artifacts. It is contemplated that the parameters of the stimulation signal (e.g., frequency, duration, waveform) provided by the stimulation subsystem 324 would be specified by other subsystems in the control module 310.

Also in the control module 310 is a memory subsystem 326 and a central processing unit (CPU) 328, which can take the form of a microcontroller. The memory subsystem 326 is coupled to the detection subsystem 322 (e.g., for receiving and storing data representative of sensed EEG signals and evoked responses), the stimulation subsystem 324 (e.g., for providing stimulation waveform parameters to the stimulation subsystem), and the CPU 328, which can control the operation of the memory subsystem 326. In addition to the memory subsystem 326, the CPU 328 is also connected to the detection subsystem 322 and the stimulation subsystem 324 for direct control of those subsystems.

The memory subsystem 326 may include one or more types of memory, including for example, random access memory (RAM), read only memory (ROM), and non-volatile memory (NVM). As explained further below, within one or more of the types of memory, such as RAM, there may be sections of memory reserved for the following: 1) EEG waveform data (stored ECoG's), 2) detailed event data regarding detection activity, 3) long-term histogram data on detections, and 4) device diagnostic information (battery voltage, lead impedance, radio usage, etc)

Also provided in the control module 310, and coupled to the memory subsystem 326 and the CPU 328, is a communication subsystem 330. The communication subsystem 330 enables communication between the implantable medical device 204 (FIG. 2) and the outside world, e.g., the data retrieval apparatus 206 (FIG. 2). The communication subsystem 330 may include a telemetry coil (which may be situated outside of the housing) enabling short-range transmission and reception of signals, to or from the implantable medical device 204, via inductive coupling. The communication subsystem 330 may also include a transceiver and one or more antennas for long-range telemetry by an RF communications link with the implantable medical device 204.

Rounding out the subsystems in the control module 310 are a power supply 332 and a clock supply 334. The power supply 332 supplies the voltages and currents necessary for each of the other subsystems. The clock supply 334 supplies substantially all of the other subsystems with any clock and timing signals necessary for their operation.

While the memory subsystem 326 is illustrated in FIG. 3 as a separate functional subsystem, the other subsystems may also require various amounts of memory to perform the functions described above and others. Furthermore, while the control module 310 is preferably a single physical unit contained within a single physical enclosure, namely the housing, it may comprise a plurality of spatially separate units each performing a subset of the capabilities described above. Also, the various functions and capabilities of the subsystems described above may be performed by electronic hardware, computer software (or firmware), or a combination thereof.

In neurostimulation, it is desirable for the stimulation delivered to a patient to be as close as possible to the amplitude or intensity settings (such as current, voltage, pulse width, etc.) with which the neurostimulator has been programmed by the physician. However, it is often the case that the neurostimulator is not capable of actually delivering what it is programmed to deliver, for example, in terms of a voltage or a current, due to battery or other hardware constraints of the active implantable medical device. For example, insufficient voltage may be available to drive a programmed amount of current through the load represented by the electrode-tissue interface. This situation is referred to here as TILT or to an "insufficient charge" condition. An insufficient charge condition may be detected using stimulation circuitry implemented in an implantable neurostimulator using means well-known in the art.

As soon as a neurostimulator recognizes that an insufficient charge condition exists, rather than curtailing the delivery of stimulation altogether or proceeding to deliver whatever stimulation the system is capable of providing, it is desirable for the system to be configured to respond to the insufficient charge circumstance in a predetermined and predictable manner. For example, when a system recognizes an insufficient charge condition, the system may be configured to deliver stimulation at a known lower amplitude setting and with other characteristics (waveform, frequency, etc.) identical to those originally programmed. This behavior may ensure that any stimulation that is provided will be safe for the patient. (Some stimulation circuitry may not otherwise deliver predictable charge-balanced pulses under an insufficient charge condition.) Further, delivering stimulation at a predetermined lower amplitude may ensure that the actual amount of stimulation delivered is a known quantity.

For instance, some neurostimulation systems are configured so that each time the neurostimulator detects a TILT or insufficient charge condition, the stimulation therapy (e.g., a burst of stimulation) will be terminated, and the system will instead deliver stimulation current at an amplitude that represents a step down from the intended (programmed current amplitude) by a small increment. If when the neurostimulator tries to deliver the stimulation with the stepped down current amplitude an insufficient charge condition is again recognized, then the system will continue to step down the current amplitude in predetermined increments until either the current amplitude reaches zero or the system no longer recognizes and insufficient charge condition. If an insufficient charge condition ceases to re-occur after a step down or sequence of step downs in the current amplitude, such that stimulation is being successfully delivered at the lower-than-programmed current amplitude, a system may be configured to periodically upwardly adjust the amplitude.

Note that the description here refers to adjustment of amplitude—which can be expressed as either voltage or current—in response to the TILT condition. However, in the presence of an insufficient charge condition, embodiments also may be configured to adjust a different stimulation waveform parameter, such as pulse width or frequency or another parameter, the value of which affects the energy or charge necessary to deliver a given stimulation waveform.

Figure 4:
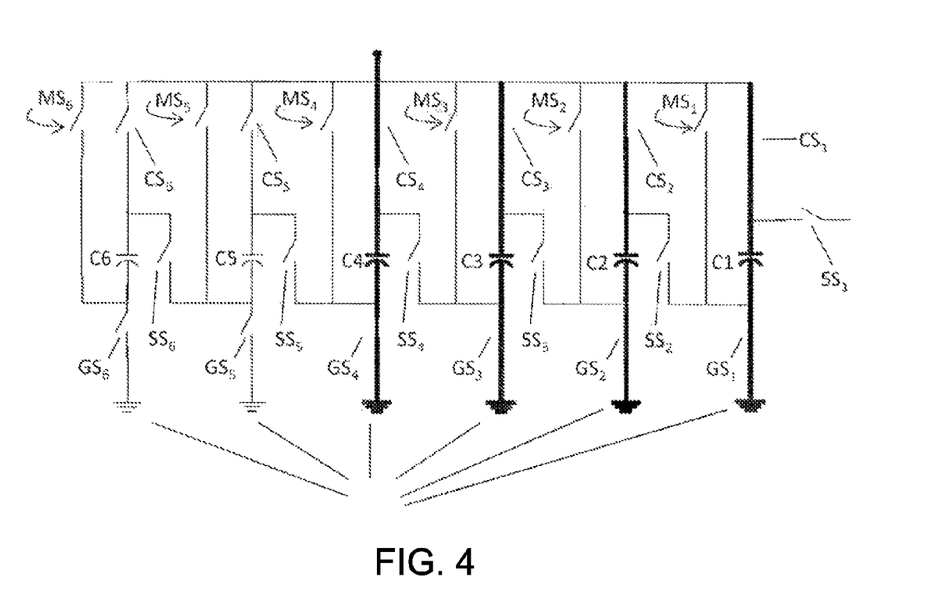
FIG. 4 is a schematic diagram of a set of capacitors in a parallel configuration for storing energy for stimulation therapy.
Figure 5:
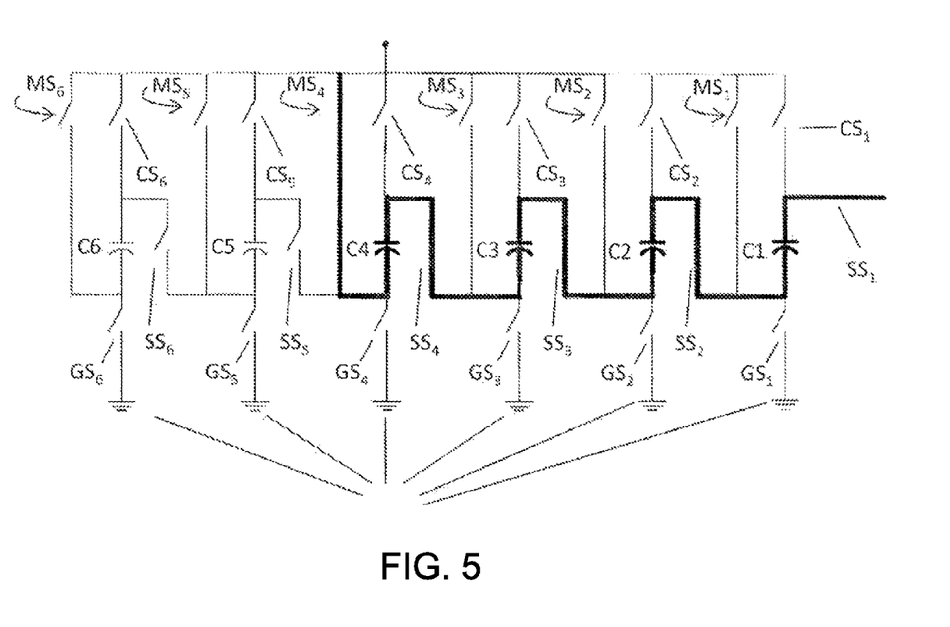
FIG. 5 is a schematic diagram of a set of capacitors in a series configuration for storing energy for stimulation therapy.

The electronic hardware used to deliver stimulation often provides several options or configurations, some of which require more energy overhead but can provide more output, others of which require less energy overhead but can provide less output. For example, in some embodiments of a neurostimulation system, current delivery is enabled by circuitry that charges a set or "stack" of capacitors. Examples of a capacitor set in a parallel arrangement and series arrangement are shown in FIGS. 4 and 5.

Each capacitor added to the stack requires more energy to charge, but makes it more likely that any given voltage can be reached and that the programmed amount of current can be delivered. The number of capacitors is referred to as a "capacitor mode" setting or parameter here. It should be appreciated that a parameter may be defined differently (i.e., other than by reference to the number of capacitors in a stack) and still govern the amount of energy available to provide stimulation.

In order to deliver as close as possible to programmed stimulation settings, while using as little energy as possible, it is desirable that the number of capacitors used be the minimum number required to support the programmed stimulation. This number can be determined manually by performing test stimulations with various capacitor configurations. A goal of minimizing energy usage can then be met by programming the neurostimulator with the lowest capacitor mode that does not result in a TILT. However, this strategy is suboptimal since (1) it is inconvenient, and (2) the ability to deliver stimulation at programmed settings can vary over the lifetime of the device depending on battery life cycle and based on changing conditions relative to other implantable components and the patient (for example, changing conditions at the interface between the patient's tissue and any stimulation delivery electrodes (e.g., provided on electrode-bearing leads), such as electrode-tissue impedance variations over time).

Therefore, embodiments of the method and system described herein provide for managing stimulation delivery and hardware settings to minimize energy use, maximizing the likelihood that programmed settings will be delivered, ensure that if programmed settings cannot be delivered then known other settings as close as possible to the programmed settings will be delivered, and minimizing the likelihood of an insufficient-charge condition.

Figure 6:
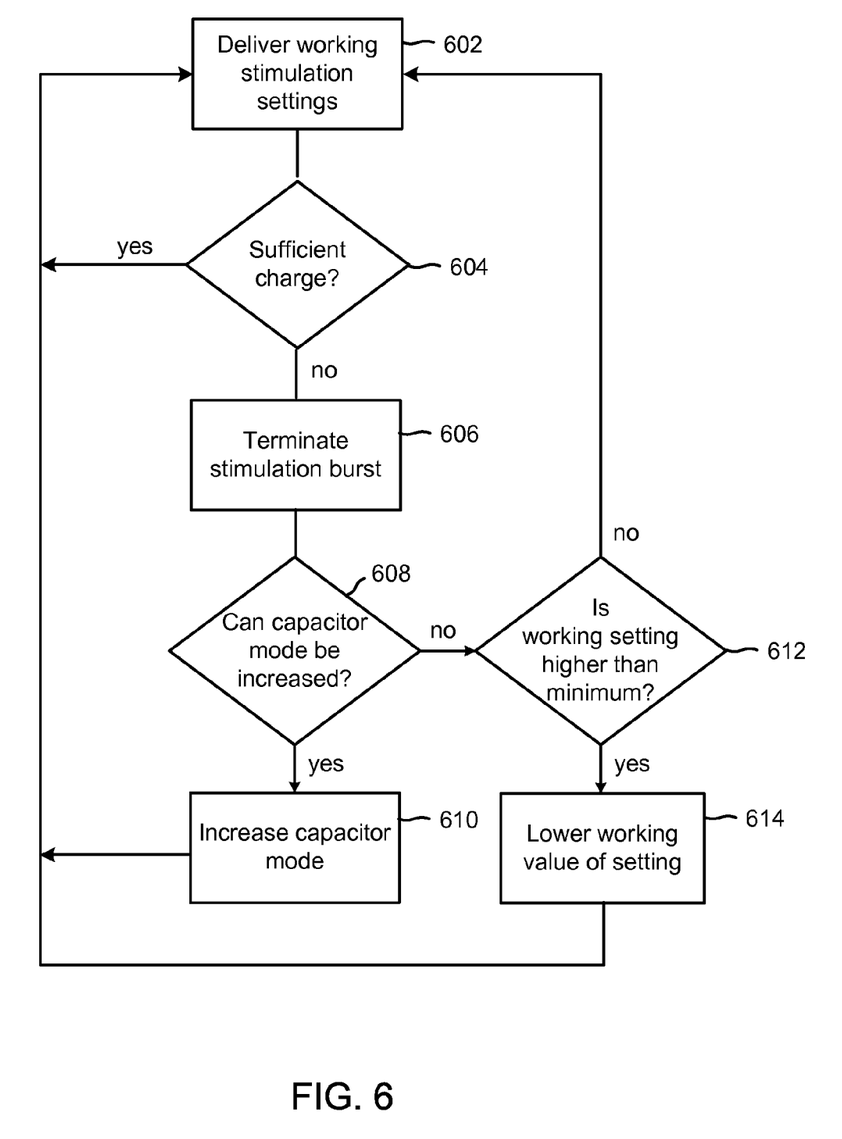
FIG. 6 is block diagram of a method for increasing energy usage and decreasing a stimulation setting, with priority given to maintaining programmed stimulation settings where possible according to embodiments.

FIG. 6 is a flow chart of a method that can be implemented by an implantable neurostimulator or other active implantable medical device to manage settings according to embodiments. When performing the method of FIG. 6, the device increases energy usage and decreases a stimulation setting, with priority given to maintaining programmed stimulation settings where possible.

At step 602 the device attempts to deliver stimulation in accordance with the working stimulation settings of the device. "Working setting" in this context means the setting of one or more parameters that characterize a stimulation at the present instance in time. As will be apparent from the following, depending on operation conditions, working settings may deviate from programmed stimulation settings. The stimulation may be in the form of a stimulation burst that includes a number of individual stimulation pulses. The working stimulation settings may define the stimulation burst in terms of burst duration, number of pulses in a burst, period between pulses and amplitude of pulses. The stimulation may be delivered using power circuitry (or stimulation circuitry) that may include the capacitor and switch circuitry shown in FIGS. 4 and 5.

Using techniques known in the art, the device at step 604 determines if the stimulation circuitry has a sufficient charge to deliver the stimulation. For example, the device may determine if the stimulation circuitry can deliver a stimulation pulse at the programmed amplitude, e.g., current amplitude. If the device has sufficient charge, the process returns to step 602. If the device does not have sufficient charge, the process proceeds to step 606 where the stimulation burst is terminated.

At step 608, the device determines if the capacitor mode can be increased. If the capacitor mode can be increased then the process proceeds to step 610, where the capacitor mode is increased. The capacitor mode may be increased by adding one or more capacitors to a series arrangement of capacitors, such as shown in FIG. 5. Upon increase of the capacitor mode, the process returns to step 602 where delivery of stimulation at the working setting is again attempted.

Returning to step 608, if the capacitor mode cannot be increased, in other words the capacitor mode has already been increased to a maximum value, the process proceeds to step 612, where the device determines if the working stimulation setting is higher than its corresponding programmed minimum. For example, a particular working stimulation setting may have a minimum amount of current delivery required in order to provide effective stimulation therapy. If the working stimulation setting is such that a current greater than the programmed minimum would be delivered (assuming a sufficient charge were available) than at step 614 the working stimulation setting is decreased. The process then returns to step 602 where subsequent stimulation is delivered with this new working setting.

Note that the term "stimulation burst" used here indicates delivery of a stimulation waveform. This waveform may be of either finite or indeterminate length (i.e., it may last until terminated by some event such as TILT or reprogramming). Conventional neurostimulation waveforms include charge-balanced biphasic pulse trains with constant frequency. However, it will be appreciate that embodiments of the systems and methods described here may be used with other waveforms such as non-charge-balanced pulse trains, DC current, frequency sweeps, pulse trains with some parameters randomly or systematically varied, and the like.

Figure 7:
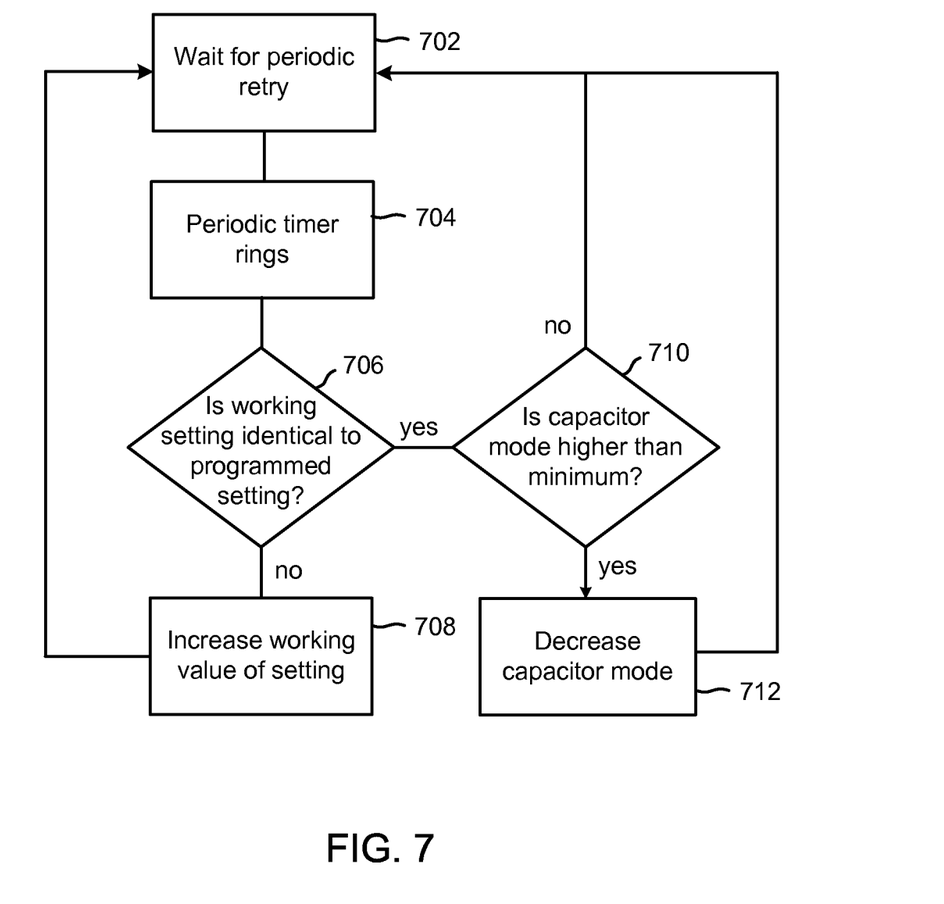
FIG. 7 is a block diagram of a method for increasing a previously decreased stimulation setting to approach a programmed setting, and for decreasing energy usage, with priority given to maintaining programmed stimulation settings where possible, according to embodiments.

FIG. 7 is a flow chart of a method that can be implemented by an implantable neurostimulator or other active implantable medical device that is meant to complement the method of FIG. 6. More specifically, the method of FIG. 7 is intended to be used at the same time as the method of FIG. 6, to further manage the implantable medical device settings in an effort to optimize power usage. When performing the method of FIG. 7, the device may increase a previously decreased working stimulation setting to approach a programmed setting, and may decrease energy usages, with priority given to maintaining programmed stimulation settings where possible.

Periodically, one or more working settings are examined by the neurostimulator to see if a working setting is lower than its corresponding programmed value due to previous insufficient charge conditions. If so, the working setting is increased and subsequent stimulation will be delivered with this new working setting. If not, the capacitor mode is examined by the neurostimulator to see if the mode is higher than a programmed minimum value. If so, the capacitor mode is decreased and subsequent stimulation will be delivered with this new capacitor mode.

More specifically, at step 702, the device waits for a periodic retry. For example, once either an increase in capacitor mode or a lowering of a working setting has occurred, such as may occur during the process of FIG. 6, the device will periodically retry to either decrease the capacitor mode or increase the working setting to return to more energy efficient settings. Upon a retry period, the process proceeds to step 704 where the device detects the end of a periodic timer. At step 706, the device determines if the present working setting is identical to the programmed setting.

If the present working setting is not identical to the programmed setting, the process proceeds to step 708 where the device increases the working setting. Because the process of FIG. 7 is predicated on a prior decrease in a working setting (step 614 of FIG. 6), the device is aware that in order to obtain a match between the present working setting and the programmed setting an increase—not a decrease—in the working setting is needed. Upon increase of the working setting, the process returns to step 702, where the device waits for the next retry period.

If the present working setting is identical to the programmed setting, the process proceeds to step 710 where the device determines if the capacitor mode is higher than a programmed minimum. If the capacitor mode is not higher than the minimum, the process returns to step 702, where the device waits for the next the next retry period. If the capacitor mode is higher than the programmed minimum, the process proceeds to step 712 where the device decreases the capacitor mode.

In addition to the benefits stated above, embodiments enable a simple process for rapid determination of the capacitor mode necessary to support programmed settings. This is of benefit for calculation of battery life, since the useful life of the charge carried by the battery will depend on how efficiently energy is used and what the capacitor mode setting is. To do this, capacitor mode, or a similar setting governing energy use, may be set to its lowest (least-energy) value at the time the neurostimulator is programmed and stimulation is enabled. With each detection of an insufficient charge condition, the capacitor mode will be automatically increased until it is sufficient to support the programmed stimulation.

A neurostimulator in which a system and method according to embodiments is implemented can report its current working settings and current capacitor mode to a host, for example a physician's programmer device. By interrogating the neurostimulator working settings and the capacitor mode parameter value for a period (e.g. several seconds to several minutes, or several stimulation bursts) after programming, the host can determine the minimum capacitor mode necessary to support the programmed settings.

In a neurostimulator that uses one instance of stimulation circuitry to deliver stimulation simultaneously across two or more stimulation paths according to two or more sets of stimulation parameters, it may not be known what set of parameters is primarily responsible for the insufficient charge condition, and therefore it is not desirable to reduce a setting uniformly across each set of parameters.

Figure 8:
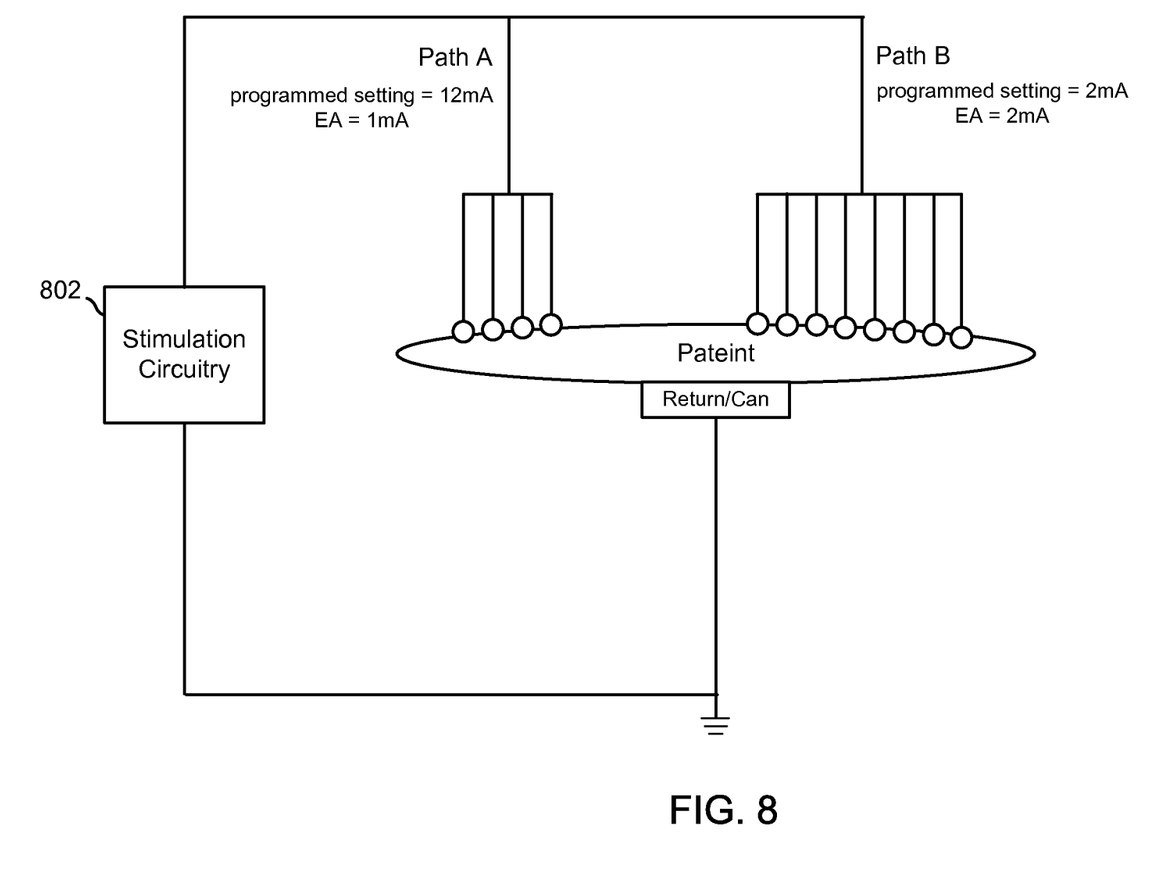
FIG. 8 is a block diagram of a power source providing stimulation along parallel paths.

For example, with reference to FIG. 8, if one instance of stimulation circuitry 802 is used to deliver monopolar stimulation at 12 mA total through four electrodes (path A) and at 2 mA total through eight electrodes (path B), then it is unlikely that path B is responsible for any insufficient charge condition that may occur, and it is desirable for the amplitude to be reduced first on path A. This determination of an insufficient charge condition may be made by the neurostimulator based on an approximate calculation of the voltage or energy required to deliver stimulation on each path. Such a calculation can be performed by the neurostimulator, optionally including estimates of impedance along the stimulation path or assuming constant impedance for each electrode involved in the path. In an embodiment particularly suited to low-power implantable devices, such a calculation can also be performed by an external component of the system (presumably with more computing power and less of a requirement to conserve power), such as the programming host. This may remove the need for the neurostimulator to perform computationally-intensive calculations such as integer or floating-point division.

Embodiments that address this problem of amplitudes on multiple stimulation paths may include use of one or more parameters titled "equivalent amplitude" (EA) to avoid unnecessary calculation. Note that a parameter is an item of data describing or specifying behavior of the neurostimulator. The EA parameters may be calculated by the programming host at the time the stimulation settings are determined, e.g. by programming, or may be calculated autonomously by the neurostimulator, e.g. when stimulation settings are programmed but before any TILT event occurs. The EA parameters, with one instance per stimulation path, indicate the reduced amplitude or amplitudes at which each stimulation path requires approximately the same amount of energy (or other limited resource such as voltage) from the stimulation circuitry.

Continuing with FIG. 8, where monopolar stimulation is being delivered at 12 mA total through four electrodes (path A) and at 2 mA total through eight electrodes (path B), and assuming each electrode on each stimulation path has approximately the same physical surface area, path B has approximately 2 times the total electrode surface area as path A. This means the voltage required to deliver a given amount of current on path A is approximately 2 times the voltage required to deliver a given amount of current on path B. Moreover, the charge density (current per unit of electrode surface area) on path A is approximately 12 times the charge density on path B. It can be seen that the charge density would be the same across both paths if amplitude were reduced to 1 mA on path A, and left at 2 mA on path B. Therefore, the EA parameters might be set to 1 mA on path A, and 2 mA on path B. Using charge density as a proxy for the amount of energy required to deliver a pulse of stimulation, this would indicate to the neurostimulator that energy requirements are approximately equal between the paths when 1 mA is delivered through path A and 2 mA is delivered through path B.

In another example (not shown), 6.0 mA total stimulation is being delivered across 3 contacts, and 11.0 mA total stimulation is being delivered across 4 contacts, with constant pulse width. In this case, the EA parameters would be set to 6.0 mA on the 3-contact path, and 8.0 mA on the 4-contact path. This would indicate to the neurostimulator that energy requirements are approximately equal between the paths when 6.0 mA is delivered on the 3-contact path and 8.0 mA is delivered on the 4-contact path.

When using EA parameters, at each insufficient charge recognition that triggers reduction of stimulation settings, any path having a programmed amplitude greater than its associated EA parameter will have its setting reduced. Paths having a programmed amplitude at or less that its associated EA parameter will not experience a change in stimulation settings. For example, with reference to FIG. 8, if the charge available at stimulation circuitry 802 is insufficient to deliver either of 12 mA to path A or 2 mA to path B, an insufficient charge condition is detected. Assuming the capacitor mode of the stimulation circuitry cannot be increased (e.g., the determination at step 608 of FIG. 6 is "no") the device determines if any of path A or path B have a programmed setting that is greater than the EA parameter of that path (e.g., the determination at step 612 of FIG. 6). In this example, path A has a programmed setting of 12 mA which is greater than its EA of 1 mA, while path B has a programmed setting that is equal to its EA. Accordingly, only the working setting of path A is reduced. When and if all working settings of amplitudes have been reduced to the corresponding EA parameter values, further insufficient charge events result in the decrease of the working setting amplitude of each path simultaneously.

Figure 9:
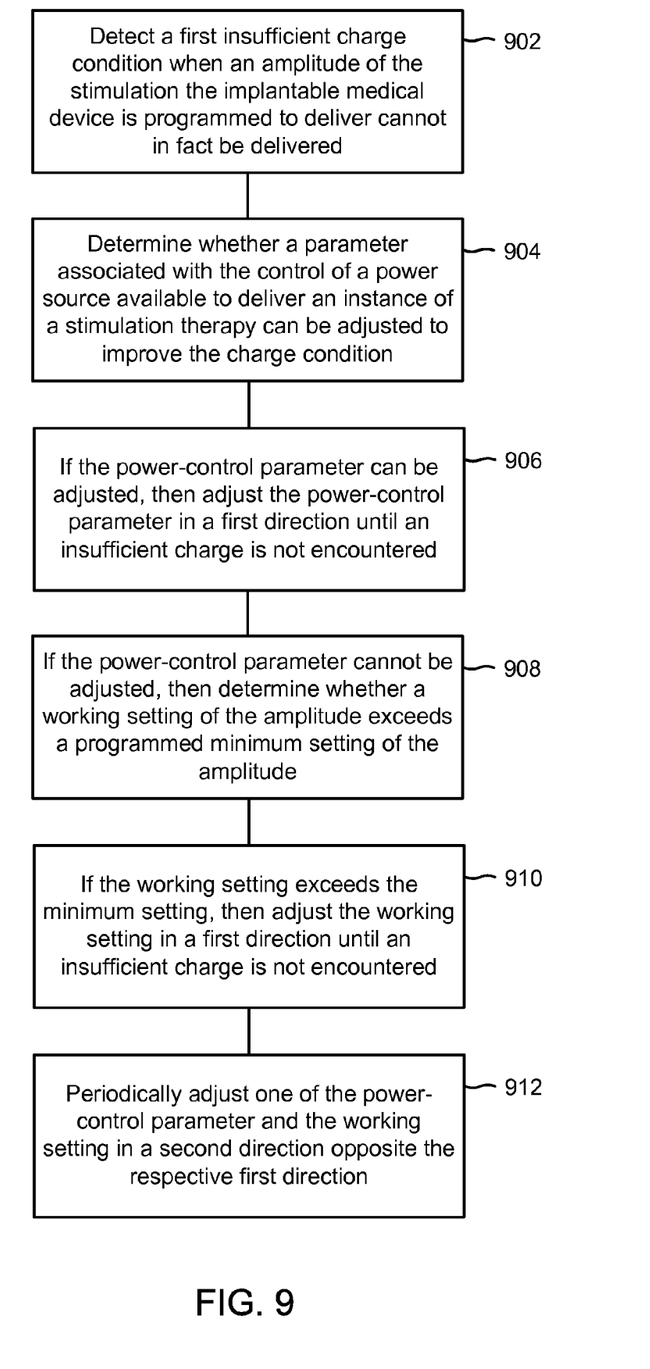
FIG. 9 is a flow chart of a method of optimizing the power used by an implantable medical device when delivering electrical stimulation to a human patient.

FIG. 9 is a flow chart of a method of optimizing the power used by an implantable medical device when delivering electrical stimulation to a human patient. The method may be performed by the implanted device. At step 902, the device detects a first insufficient charge condition when an amplitude of the stimulation the implantable medical device is programmed to deliver cannot in fact be delivered. At step 904, the device determines whether a parameter associated with the control of a power source available to deliver an instance of a stimulation can be adjusted to improve the charge condition.

If the power-control parameter can be adjusted, then at step 906, the device adjusts the power-control parameter in a first direction until an insufficient charge is not encountered. The power-control parameter may be a capacitor mode parameter that corresponds to a number of capacitors used to provide the power for any given instance of stimulation therapy. In this case, the first direction of the power-control parameter corresponds to an increase in the number of capacitors.

If the power-control parameter cannot be adjusted, then at step 908, the device determines whether a working setting of the amplitude exceeds a programmed minimum setting of the amplitude. If the working setting exceeds the minimum setting, then at step 910, the device adjusts the working setting in a first direction until an insufficient charge is not encountered. The first direction of the working setting may correspond to a decrease in the working setting. For example, if the working setting relates to an amount of current to be delivered, the current may be decreased.

At step 912, the device periodically adjusts one of the power-control parameter and the working setting in a second direction opposite the respective first direction. Adjustments in the second direction may be performed until another insufficient charge is encountered. In some instances, the working setting is adjusted in the second direction when the working setting is different from the programmed minimum setting. In other instances, the power-control parameter is adjusted in the second direction when the working setting is identical to the programmed minimum setting and the power-control parameter exceeds a programmed minimum.

Figure 10:
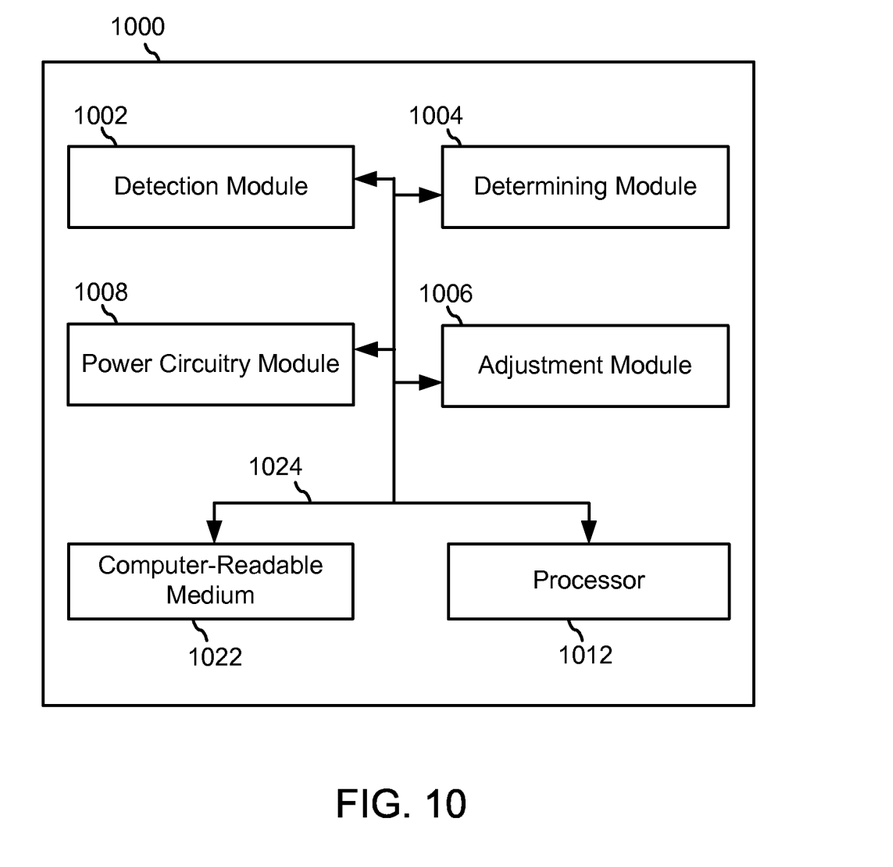
FIG. 10 is a block diagram of a processing system that implements the method of FIG. 9.

FIG. 10 is a diagram illustrating an example of a hardware implementation for an active implantable medical device employing a processing system 1000. The processing system 1000 may be implemented with a bus architecture, represented generally by the bus 1024. The bus 1024 links together various circuits including one or more processors and/or hardware modules, represented by a processor 1012, a detection module 1002, a determining module 1004, an adjustment module 1006, a power circuitry module 1008, and a computer-readable medium/memory 1022. The processor 1012 may correspond to the CPU 328 of FIG. 3.

The detection module 1002 detects a first insufficient charge condition when an amplitude of the stimulation therapy output by the power circuitry is insufficient to deliver a programmed stimulation. The determining module 1004 determines whether a parameter associated with the control of the power circuitry module 1008 can be adjusted to improve the charge condition. If the power-control parameter cannot be adjusted, then the determining module 1004 determines whether a working setting of the amplitude exceeds a programmed minimum setting of the amplitude.

Based on one or more determinations of the determining module 1004, the adjustment module 1006 performs adjustments of one or more parameters or setting. For example, if the power-control parameter can be adjusted, then the adjustment module 1006 adjusts the power-control parameter in a first direction until an insufficient charge is not encountered. If the working setting exceeds the minimum setting, then the adjustment module 1006 adjusts the working setting in a first direction until an insufficient charge is not encountered. The adjustment module 1006 also periodically adjusts one of the power-control parameter and the working setting in a second direction opposite the respective first direction.

These modules may be included in circuitry and components described above. For example, one or more of the detection module 1002, the determining module, the adjustment module 1006 and the power circuitry module 1008 may be included in the stimulation subsystem 324 and/or power supply 332 of FIG. 3. The processor 1012 and computer-readable medium 1022 may be included in the memory subsystem 326 and CPU 328, respectively.

The processor 1012 is responsible for general processing, including the execution of software stored on the computer-readable medium/memory 1022. The software, when executed by the processor 1012, causes the processing system 1000, including the detection module 1002, the determining module, the adjustment module 1006 and the power circuitry module 1008, to perform the various functions described above with respect to FIGS. 6, 7, and 9.

The efficient use of power is a common design concern for many different types of active implantable devices the power sources or reserves of which are limited (e.g., primary cell or rechargeable battery). Such active implantable devices may include pacemakers or devices intended to stimulate the stomach or bladder. Thus, the use of the term "neurostimulation" herein is not intended to limit applicability of embodiments to neural tissue in the brain.

Disclosed herein is a method for optimizing the power used by an implantable medical device when delivering electrical stimulation to a human patient, comprising. The method is implemented with electronic circuitry in an implantable medical device. The method includes recognizing a first insufficient charge condition when an amplitude of the stimulation the implantable medical device is programmed to deliver cannot in fact be delivered to a patient. In response to the first insufficient charge condition, the method automatically adjusting in a first direction a parameter associated with the control of a power source available to deliver an instance of a stimulation therapy until an insufficient charge is not encountered. Whenever an insufficient charge condition is not encountered, the method includes periodically adjusting in a second direction opposite the first direction the power-source-controlling parameter until another insufficient charge is encountered or until a maximum power reservoir has been reached or exceeded. The power-source-controlling parameter may be a capacitor mode parameter and corresponds to a number of capacitors that will be used to provide the power for any given instance of stimulation therapy.

It should be noted that there can be a variety of ways in which systems and methods according to embodiments may be implemented. For example, software, hardware (including ASICs, FPGAs, and other custom electronics), and various combinations of software and hardware, are all solutions that would be possible to practitioners of ordinary skill in the art of electronics and systems design. It should further be noted that the methods described herein may be performed in software and/or hardware: hardware may be preferable in some instances to reduce computational load on the processor of the active implantable medical device. Various embodiments may be carried out by processors and electrical components under the control of computer readable and computer executable instructions. The computer readable and computer executable instructions reside, for example, in a non-transitory data storage medium such as computer usable volatile and non-volatile memory. However, the computer readable and computer executable instructions may reside in any type of non-transitory computer readable storage medium.

The various aspects of this disclosure are provided to enable one of ordinary skill in the art to practice the present invention. Various modifications to exemplary embodiments presented throughout this disclosure will be readily apparent to those skilled in the art, and the concepts disclosed herein may be extended to other magnetic storage devices. Thus, the claims are not intended to be limited to the various aspects of this disclosure, but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

The invention claimed is:

1. A method of optimizing the power used by an implantable medical device when delivering electrical stimulation to a human patient, comprising:
    detecting a first insufficient charge condition when an amplitude of the stimulation the implantable medical device is programmed to deliver cannot in fact be delivered;
    determining whether a parameter associated with the control of a power source available to deliver an instance of a stimulation can be adjusted to improve the charge condition;
    if the power-control parameter can be adjusted, then adjusting the power-control parameter in a first direction until an insufficient charge is not encountered;
    if the power-control parameter cannot be adjusted, then determining whether a working setting of the amplitude exceeds a programmed minimum setting of the amplitude; and
    if the working setting exceeds the minimum setting, then adjusting the working setting in a first direction until an insufficient charge is not encountered.

2. The method of claim 1, wherein the power-control parameter is a capacitor mode parameter that corresponds to a number of capacitors used to provide the power for any given instance of stimulation.

3. The method of claim 2, wherein the first direction of the power-control parameter corresponds to an increase in the number of capacitors.

4. The method of claim 1, wherein the first direction of the working setting corresponds to a decrease in the working setting.

5. The method of claim 1, further comprising periodically adjusting one of the power-control parameter and the working setting in a second direction opposite the respective first direction.

6. The method of claim 5, wherein the adjusting in the second direction is performed until another insufficient charge is encountered.

7. The method of claim 5, wherein the working setting is adjusted in the second direction when the working setting is different from the programmed minimum setting.

8. The method of claim 5, wherein the power-control parameter is adjusted in the second direction when the working setting is identical to the programmed minimum setting and the power-control parameter exceeds a programmed minimum.

9. An active implantable medical device, comprising:
    power circuitry configured to output stimulation; and a processor coupled the power circuitry and configured to:
- detect a first insufficient charge condition when an amplitude of the stimulation output by the power circuitry is insufficient to deliver a programmed stimulation;
- determine whether a parameter associated with the control of the power circuitry can be adjusted to improve the charge condition;
- if the power-control parameter can be adjusted, then adjust the power-control parameter in a first direction until an insufficient charge is not encountered;
- if the power-control parameter cannot be adjusted, then determine whether a working setting of the amplitude exceeds a programmed minimum setting of the amplitude; and
- if the working setting exceeds the minimum setting, then adjust the working setting in a first direction until an insufficient charge is not encountered.

10. The device of claim 9, wherein the power-control parameter is a capacitor mode parameter that corresponds to a number of capacitors of the power circuitry, the capacitors used to provide the power for any given instance of stimulation.

11. The device of claim 10, wherein the first direction of the power-control parameter corresponds to an increase in the number of capacitors.

12. The device of claim 9, wherein the first direction of the working setting corresponds to a decrease in the working setting.

13. The device of claim 9, wherein the processor is further configured to periodically adjust one of the power-control parameter and the working setting in a second direction opposite the respective first direction.

14. The device of claim 13, wherein adjustments in the second direction are performed until another insufficient charge is encountered.

15. The device of claim 13, wherein the working setting is adjusted in the second direction when the working setting is different from the programmed minimum setting.

16. The device of claim 13, wherein the power-control parameter is adjusted in the second direction when the working setting is identical to the programmed minimum setting and the power-control parameter exceeds a programmed minimum.

17. A method for optimizing the power used by an implantable medical device when delivering electrical stimulation to a human patient, comprising:
- recognizing a first insufficient charge condition when an amplitude of the stimulation the implantable medical device is programmed to deliver cannot in fact be delivered to a patient;
- in response to the first insufficient charge condition, adjusting in a first direction a parameter associated with the control of a power source available to deliver an instance of a stimulation therapy until an insufficient charge is not encountered; and
- whenever an insufficient charge condition is not encountered, periodically adjusting in a second direction opposite the first direction the power-source-controlling parameter until another insufficient charge is encountered or until a maximum power reservoir has been reached or exceeded.

18. The method of claim 17 wherein the power-source-controlling parameter is a capacitor mode parameter and corresponds to a number of capacitors that will be used to provide the power for any given instance of stimulation therapy.

* * * * *